United States Patent [19]

Miyake et al.

[11] Patent Number: 4,861,929
[45] Date of Patent: Aug. 29, 1989

[54] PROCESS FOR PRODUCING HALOGENATED BENZENE DERIVATIVE USING ZEOLITE CATALYST

[75] Inventors: Takanori Miyake; Kazuhiko Sekizawa; Toshio Hironaka; Yukihiro Tsutsumi, all of Yamaguchi, Japan

[73] Assignee: Tosoh Corporation, Yamaguchi, Japan

[21] Appl. No.: 947,306

[22] Filed: Dec. 29, 1986

[30] Foreign Application Priority Data

Dec. 27, 1985 [JP] Japan ............................ 60-292431
Jan. 20, 1986 [JP] Japan .............................. 61-7832

[51] Int. Cl.[4] .............................................. C07C 17/12
[52] U.S. Cl. .................................. 570/209; 570/206; 570/208
[58] Field of Search ............... 570/197, 198, 208, 209, 570/210, 206, 207

[56] References Cited

U.S. PATENT DOCUMENTS

| | | | |
|---|---|---|---|
| 1,946,040 | 2/1934 | Stoesser et al. | 570/208 |
| 3,226,447 | 12/1965 | Bing et al. | 570/208 |
| 3,499,941 | 3/1970 | Givens et al. | 570/208 |
| 4,031,146 | 6/1977 | DiBella | 570/209 |
| 4,092,369 | 5/1978 | Gelfand | 570/208 |

FOREIGN PATENT DOCUMENTS

| | | | |
|---|---|---|---|
| 0112722 | 7/1984 | European Pat. Off. | 570/208 |
| 0118851 | 9/1984 | European Pat. Off. | 570/208 |
| 0171265 | 2/1986 | European Pat. Off. | 570/208 |
| 0031627 | 2/1982 | Japan | 570/208 |
| 0144722 | 8/1984 | Japan | 570/208 |
| 0224644 | 11/1985 | Japan | 570/208 |
| 0650985 | 3/1979 | U.S.S.R. | 570/208 |
| 0956443 | 9/1982 | U.S.S.R. | 570/208 |
| 1153746 | 9/1966 | United Kingdom | 570/208 |
| 1490677 | 11/1977 | United Kingdom | 570/208 |

OTHER PUBLICATIONS

Wortel et al., "Selective Bromination of Halobenzenes, Etc.," J. Catalysis, vol. 60, pp. 110–120 (1979).
Huizinga et al., "Zeolite ZSM-5 and Related Materials, Etc.," Tetrahedron Letters, vol. 21, pp. 3809–3812 (1980).
Onaka et al., "Selective Monobromination of Aniline Derivatives, Etc.", Chemistry Letters, pp. 2007–2008 (Chemical Soc'y of Japan, 1984).

Primary Examiner—Werren B. Lone
Attorney, Agent, or Firm—Sughrue, Mion, Zinn, Macpeak & Seas

[57] ABSTRACT

A p-substituted halobenzene derivative, which is very valuable in industry, can be obtained by halogenation of benzene and/or a benzene derivative in the liquid phase using, as a catalyst, a faujasite type zeolite in the presence of any one member selected from the group consisting of sulfur-containing compounds, nitrogen-containing organic basic compounds, salts of said nitrogen-containing organic basic compounds, and a mixture of said nitrogen-containing organic basic compounds and salts thereof.

8 Claims, No Drawings

PROCESS FOR PRODUCING HALOGENATED BENZENE DERIVATIVE USING ZEOLITE CATALYST

BACKGROUND OF THE INVENTION

1. Field of the Invention

The present invention relates to a process for producing a halogenated benzene derivative by halogenating benzene and/or a benzene derivative in the liquid phase. More particularly, the present invention relates to a process for selectively producing a p-substituted halobenzene derivative by halogenating benzene and/or a benzene derivative in the liquid phase using, as a catalyst, a faujasite type zeolite in the presence of any one member selected from the group consisting of sulfur-containing compounds, nitrogen-containing organic basic compounds, salts of said nitrogen-containing organic basic compounds, and a mixture of said nitrogen-containing organic basic compounds and salts thereof.

2. Description of the Prior Art

Halogenated benzene derivatives are important raw materials or intermediates in various fields such as medicines, agricultural chemicals and organic synthesis chemistry. They are ordinarily produced by halogenating benzene and/or a benzene derivative in the liquid phase using, as a catalyst, a Lewis acid such as ferric chloride, antimony chloride or the like. For instance, dichlorobenzene (hereinafter abbreviated to DCB) is produced by blowing chlorine gas into benzene or monochlorobenzene (hereinafter abbreviated to MCB) in the presence of ferric chloride.

As is well known, in the production of a di-substituted benzene derivative by the liquid phase halogenation of a mono-substituted benzene derivative, three isomers, namely, a 1,2-di-substituted benzene derivative (an o-isomer), a 1,3-di-substituted benzene derivative (an m-isomer) and a 1,4-di-substituted benzene derivative (a p-isomer) are formed as products. The proportions of these isomers are decided by the kind of existing substituent on the mono-substituted benzene derivative, the kind of catalyst used, etc. For instance, in the production of DCB by liquid phase chlorination of MCB in the presence of ferric chloride, the following three isomers are formed in the following proportions.

| | |
|---|---|
| o-Dichlorobenzene | 30 to 40% |
| m-Dichlorobenzene | 0 to 5% |
| p-Dichlorobenzene | 60 to 70% |

In the three isomers of di-substituted halobenzene derivatives, p-substituted halobenzene derivatives are in the greatest demand and are most important industrially. Hence, a number of processes have hitherto been proposed for the selective production of p-substituted halobenzene derivatives.

These prior arts include processes for selectively producing a p-substituted halobenzene derivative by halogenating benzene and/or a benzene derivative using a zeolite as a catalyst in place of a Lewis acid. For instance, "Journal of Catalysis" 60, 110 (1979) describes the use of zeolite as a catalyst for bromination of a halogenated benzene. In this literature, it is indicated that a p-substituted bromobenzene derivative can be produced selectively by using, as a bromination catalyst, various ion-exchanged X type and Y type zeolites.

Further, "Tetrahedron Letters" 21, 3809 (1980) describes the chlorination of benzene using various catalysts such as ZSM-5, ZSM-11, mordenite, L type zeolite and Y type zeolite. It is indicated in this literature that L type zeolite, in particular, can produce p-dichlorobenzene (hereinafter abbreviated to PDCB) at a high selectivity. Furthermore, Japanese Patent Public Disclosure (Laid-Open) Publication) Nos. 130227/1984, 144722/1984 and 163329/1984, for example, disclose processes for halogenating benzene or an alkylbenzene using L type zeolite or Y type zeolite as a catalyst.

It is known that, the selectivity of a p-substituted halobenzene derivatives is improved, if one of the various sulfur-containing compounds is added as a cocatalyst into the reaction system, where a Lewis acid such as ferric chloride is used as a catalyst. For instance, U.S. Pat. No. 3,226,447 states that in chlorination of benzene, MCB or the like, a p-substituted halobenzene derivative can be produced at a higher selectivity by adding an organic sulfur compound containing divalent sulfur to a Lewis acid catalyst (e.g., ferric chloride). More specifically, it is indicated in this cited literature that, if chlorination of benzene is effected using iron and thioglycolic acid as catalysts, the proportion of PDCB in the produced DCB reaches 77%. In addition, U.S. Pat. No. 1,946,040 and British Pat. No. 1,153,746, for example, disclose processes for producing a p-substituted halobenzene derivative using sulfur or an organic sulfur compound as a catalyst, together with a Lewis acid catalyst such as ferric chloride, antimony trichloride or the like, in chlorination of an alkylbenzene or the like. Further, it is described in Chemistry Letters, pp. 2007–2008, (1984) that in bromination of aniline using A type zeolite having bromine adsorbed thereon, addition of pyridine or 2,6-lutidine improves brominating activity and the selectivity of para-bromoaniline.

However, it is known to those skilled in the art that a Lewis acid catalyst is essential for the above-described known processes.

It is obvious from the prior arts that in halogenation of benzene and/or a benzene derivative, processes using a zeolite catalyst can produce a p-substituted halobenzene derivative at a higher selectivity than conventional processes using a Lewis acid catalyst (e.g., ferric chloride).

However, the selectivity of a p-substituted halobenzene derivative in the said prior art processes which use a zeolite catalyst is still insufficient from the industrial viewpoint. Accordingly, it is desired to develop a process for producing a p-substituted halobenzene derivative at an enhanced selectivity.

In view of the above-described circumstances, the present inventors examined in detail the processes for selectively producing a p-substituted halobenzene derivative by liquid phase halogenation of benzene and/or a benzene derivative, and particularly, directed their attention to halogenation reactions which use a zeolite as a catalysts.

As a result, the present inventors found that, if halogenation of benzene and/or a benzene derivative is carried out using a faujasite type zeolite as a catalyst in the presecce of any one member selected from the group consisting of sulfur-containing compounds, nitrogen-containing organic basic compounds, salts of said nitrogen containing organic basic compounds and a mixture of said nitrogen-containing organic basic compounds and salts thereof, the ratio of produced di-substituted isomers surprisingly enough changes with no substantial lowering of activities, and the selectivity of a p-substituted halobenzene derivative is enhanced.

As described above, it is known that, when a Lewis acid such as ferric chloride is used as a catalyst in halogenation of benzene and/or a benzene derivative, addition of a sulfur-containing compound as a cocatalyst enhances the selectivity of a p-substituted halobenzene derivative. It is considered that such advantageous effect is made available by the fact that the Lewis acid is modified by the sulfur-containing compound. More specifically, in the liquid phase halogenation using a Lewis acid catalyst, the Lewis acid is dissolved in a reaction mixture to perform a catalytic reaction in a homogeneous system, and therefore it is estimated that a sulfur-containing compound, which is similarly dissolved in the reaction mixture changes the properties of the Lewis acid by, for example, coordination.

On the other hand, in the liquid phase halogenation using a zeolite catalyst, the zeolite is not dissolved in the reaction mixture, and acts as a heterogeneous catalyst. Therefore, the working mechanism of the zeolite catalyst is completely different from that of a Lewis acid catalyst. Further, the advantageous effect which is offered by a zeolite catalyst in the presence of a sulfur-containing compound is particularly unique to faujasite type zeolites. Accordingly, the effect obtained by the presence of a sulfur-containing compound is completely different from the cocatalytic effect thereof in the case of a reaction using a Lewis acid catalyst. Thus, the present invention has been accomplished on the basis of the finding of this new fact. In addition, it is known, as described above, that in bromination of aniline using A type zeolite having bromine adsorbed thereon, addition of pyridine or 2,6-lutidine enables both brominating activity and the selectively of para-bromoaniline to be enhanced. However, there is no suggestion in the cited literature that a compound such as pyridine is effective in improving liquid phase halogenation of benzene and/or a benzene derivative using a faujasite type zeolite.

SUMMARY OF THE INVENTION

It is therefore an object of the present invention to provide a process for producing a halogenated benzene derivative by halogenating benzene and/or a benzene derivative in the liquid phase using, as a catalyst, a faujasite type zeolite in the presence of any one member selected from the group consisting of sulfur-containing compounds, nitrogen-containing organic basic compounds, salts of said nitrogen-containing organic basic compounds, and a mixture of said nitrogen-containing organic basic compounds and salts thereof.

Other objects and advantages of the present invention will become apparent to those skilled in the art from the following description and disclosure.

DETAILED DESCRIPTION OF THE PREFERRED EMBODIMENT

The present invention uses a zeolite catalyst. Zeolite is commonly known as a crystalline aluminosilicate. It has a structure consisting of $SiO_4$ tetrahedrons and $AlO_4$ tetrahedrons. Various types of zeolite are known depending upon the type of bonding of these tetrahedrons. In the process according to the present invention, a faujasite type zeolite is employed as a catalyst. Faujasite type zeolites are present in nature but can also be synthesized according to known processes. Synthetic faujasite type zeolites are widely known as X type and Y type zeolites. In the present invention, it is preferable to employ a synthetic faujasite type zeolite which contains less impurities and has a high degree of crystallinity. Particularly the Y type zeolite is preferable. Each zeolite has a different crystal structure and therefore can be identified by means of X-ray diffractometry (powder method).

Typical faujasite type zeolite has the following formula when expressed in the mole ratio of oxides:

$aM_{2/n}O \cdot Al_2O_3 \cdot bSiO_2$ (wherein $a=1.0\pm0.3$, $b=2$ to 8, and n is the valency of a cation M). Synthetic faujasite type zeolites, that is, X type and Y type zeolites generally contain Na ion as the cation M, when they are synthesized.

In the present invention, the cation contained in faujasite type zeolite has no particular restriction. Therefore, a synthesized faujasite zeolite which contains Na ion can be used as it is. However, a faujasite type zeolite obtained by ion-exchanging of Na for other cation can also be used, if necessary. This ion-exchange treatment may be effected, for example, by an aqueous solution containing a desired cation, according to a known method.

In the process of the present invention, various kinds of ion exchanged faujasite type zeolites may be used as catalysts as they are. It is, however, preferable to employ the faujasite type zeolite which has been modified by a metal salt. Modification of a faujasite type zeolite by a metal salt can be effected simply by, for example, bringing them into uniform and close contact with each other. Practical examples of methods for this modification include ordinary impregnation, mixing and kneading methods. Although there is no particular restriction on the method used for modification by a metal salt, it is preferable to employ an ordinary impregnation in which a metal salt is dissolved in any desired solvent, e.g., water, and a faujasite type zeolite is dipped in this solution so as to be impregnated with the metal salt. Since this method enables not only the outer surfaces of grains of the faujasite type zeolite but also the inner surfaces of pores in the zeolite to be modified uniformly and intimately, and can readily be carried out.

There is no particular restriction with regard to the metal salt used for modification, and it is possible to employ halides, sulfates, carbonates, etc. of alkaline metals, alkaline earth metals, rare earth metals and the like. Examples of metal salts which may be employed in the present invention include sodium chloride, potassium chloride, strontium chloride, barium chloride, lanthanum chloride, sodium carbonate, potassium carbonate, strontium carbonate, barium carbonate, sodium sulfate, potassium sulfate, strontium sulfate and barium sulfate.

The amount of a metal salt used for modification may be 0.1 to 90%, preferably 10 to 80%, when expressed in terms of the weight percent with respect to the weight of the faujasite type zeolite employed.

In the present invention, the shape of the catalyst is not particularly restricted. Ordinarily, the catalyst is used after being molded into a desired shape but it may of course be used in a powder form. Molding can be conducted according to an ordinary method such as extrusion molding, tablet molding, spray-drying granulating molding or the like. In molding, substances which are inert to the halogenation reaction can be added as a binder or a molding aid in order to enhance the mechanical strength of the molding obtained. For example, substances such as silica, clay, graphite, stearic acid, starch, polyvinyl alcohol and the like can be added in an amount of 0 to 80% by weight, preferably 2 to 30% by weight.

The catalyst thus obtained is then dried, if necessary, and calcined before being used in the liquid phase halogenation. The calcination is conducted for 10 minutes to 24 hours at 200° to 900° C., preferably 300° to 850° C. in a flow of air or an inert gas such as nitrogen or helium.

In the process according to the present invention, the liquid phase halogenation of benzene and/or a benzene derivative is carried out in the presence of any one member selected from the group consisting of sulfur-containing compounds, nitrogen-containing organic basic compounds, salts of said nitrogen-containing organic basic compounds and a mixture of said nitrogen-containing organic basic compounds and salts thereof. Sulfur-containing compounds in this case include sulfur, inorganic compounds containing a divalent sulfur atom, that is, a sulfur atom having two bond valences, and organic compounds containing sulfur. The bond valence refers to the number of valences with which one sulfur atom is attached to another atom (including another sulfur atom). When employing an inorganic compound containing a divalent sulfur atom, it is preferable to select a compound which consists of a non-metallic element, e.g., hydrogen or an element selected from among those belonging to the carbon, nitrogen and halogen groups in the periodic table, and a divalent sulfur atom.

Examples of such inorganic compounds include sulfur, sulfur monochloride, sulfur dichloride, sulfur monobromide, carbon disulfide, hydrogen sulfide, silicon disulfide, sulfur nitrides and phosphorus sulfides. Sulfur, sulfur monochloride and sulfur dichloride are particularly preferable.

Examples of sulfur-containing organic compounds include mercaptans such as methyl mercaptan, ethyl mercaptan, propyl mercaptan and phenyl mercaptan; sulfides such as dimethyl sulfide, diethyl sulfide and diphenyl sulfide; thiophenes such as thiophene, methyl thiophene and chlorothiophene; disulfides such as dimethyl disulfide and diphenyl disulfide; sulfoxides such as dimethyl sulfoxide and diphenyl sulfoxide; and sulfones such as dimethyl sulfone and diphenyl sulfone. Particularly preferable are sulfides such as diphenyl sulfide, thiophenes such as thiophene, sulfoxides such as diphenyl sulfoxide and sulfones such as diphenyl sulfone.

A sulfur-containing compound selected from among those described above is only required to be present in a solution for liquid phase halogenation reaction, and there is no particular restriction on the mixing method or the like.

More specifically, a sulfur-containing compound may be added into the reaction system composed of the raw material and the catalyst, or may be introduced into the reaction system after being adsorbed or carried on a faujasite type zeolite. In a continuous reaction, a sulfur-containing compound may be contained in a raw material, e.g., a sulfur-containing compound may be dissolved in the raw material, and supplied into the reaction system, together with the raw material.

It is difficult to unconditionally limit the amount of sulfur-containing compound employed, since there are a great variety of sulfur-containing compounds available and the amount varies depending upon, for example, the mixing method used. It is, however, possible to specify the amount of sulfur-containing compound in terms of the weight of sulfur atom contained in the reaction mixture employed. The amount of sulfur atom contained in sulfur-containing compounds employed in the present invention is preferably from $1 \times 10^{-4}$ gram to 1.0 gram per gram of the faujasite type zeolite catalyst, more preferably from $1 \times 10^{-3}$ gram to 0.5 gram per gram of the faujasite type zeolite catalyst. When the amount is less than $1 \times 10^{-4}$ gram per gram of the faujasite type zeolite catalyst, the selectivity of a p-substituted halobenzene derivative cannot effectively be improved, whereas, when the amount is more than 1.0 gram per gram of the faujasite type zeolite catalyst, the effect of increase in the amount of catalyst is small and is therefore uneconomical.

Nitrogen-containing organic basic compounds employed in the present invention include organic compounds which contain a nitrogen atom in their molecules and whose basicity constant $K_b$ measured in water at 25° ranges from $1 \times 10^{-14}$ to $1 \times 10^{-1}$. Salts of nitrogen-containing organic basic compounds mean compounds formed through reaction between nitrogen-containing organic basic compounds and mineral acids such as hydrogen chloride and hydrogen bromide.

Nitrogen-containing heterocyclic compounds and/or salts thereof and amine compounds and/or salts thereof are preferable examples of the nitrogen-containing organic basic compounds and salts of these compounds which may be employed in the present invention.

Examples of nitrogen-containing hetrocyclic compounds and salts thereof include pyrroles such as pyrrole, methylpyrrole and indole; pyrazoles such as pyrazole and methylpyrazole; imidazoles such as imidazole, benzoimidazole and phenylimidazole; pyrrolines such as pyrroline and methylpyrroline; pyrrolidines such as pyrrolidine and methylpyrrolidine; pyridines such as pyridine, picoline, lutidine, ethylpyridine and chloropyridine; pyrazines such as pyrazine and methylpyrazine; pyrimidines such as pyrimidine and methylpyrimidine; piperazines such as piperazine and methylpiperazine; piperidines such as piperidine and methylpiperidine; quinolines such as quinoline, methylquinoline, dimethylquinolin, benzoquinoline, oxyquinoline and chloroquinoline; isoquinolines such as isoquinoline, methylisoquinoline and chloroisoquinoline; indolizines; 4H-quinolizines; cinnolines; quinozolines; carbazoles; acridines; phenazines; phenanthridines; and salts of these compounds. Particularly preferable are imidazoles such as phenylimidazole; pyridines such as pyridine; quinolines such as quinoline, methylquinoline, dimethylquinoline and oxyquinoline; isoquinolines such as isoquinoline; and salts of these compounds.

Amine compounds are compounds in which a hydrogen atom of ammonia is replaced by a hydrocarbon substituent, and are classified into three kinds, namely, primary, secondary and tertiary amines, in accordance with the number of substituted hydrogen atoms. Examples of amine compounds and salts thereof include: as aliphatic amines, aliphatic primary amines such as methylamine, ethylamine, propylamine, isopropylamine, butylamine, isobutylamine, tert-butylamine, amylamine, hexylamine, palmitylamine, ethylenediamine and monoethanolamine; aliphatic secondary amines such as dimethylamine, diethylamine, dipropylamine, dibutylamine, diamylamine and diethanolamine; and aliphatic tertiary amines such as trimethylamine, triethylamine, tripropylamine, tributylamine, triamylamine and N,N-dimethylamine, as aromatic amines, aromatic primary amines such as aniline and naphthylamine; aromatic secondary amines such as diphenylamine and N-methylaniline; and aromatic tertiary amines such as N,N-dimethylaniline and p-dimethylaminoazobenzene; and salts of these compounds. In the present invention, it suffices to use at least one substance selected from among these nitrogen-containing organic basic compounds and salts thereof.

In the present invention, it is only necessary for at least one substance selected from among the above-described nitrogen-containing organic basic compounds and their salts to be present in a reaction mixture for the liquid phase halogenation reaction, and there is no particular restriction on the mixing method and the like. More specifically, at least one substance selected from among the above-described nitrogen-containing compounds and their salts may be added into the reaction system composed of the raw material and the catalyst, or may be introduced into the reaction system after being adsorbed or carried on the faujasite type zeolite catalyst. In a continuous reaction, at least one substance selected from among the above-described nitrogen-containing compounds and their salts may be contained in the raw material, e.g., it may be dissolved in the raw material in the liquid phase, and then supplied into the reaction system together with the raw material.

It is difficult to unconditionally limit the amount of the at least one substance selected from among the above-described nitrogen-containing compounds and their salts, since there are a great variety of nitrogen-containing compounds and their salts available and said amount will vary depending upon, for example, the mixing method used. It is, however, possible to specify the amount in terms of the weight of nitrogen atom contained in the reaction mixture. The amount of nitrogen atom containing in nitrogen-containing organic basic compounds and/or salts thereof employed in the present invention is from $1 \times 10^{-4}$ gram to 0.5 gram per gram of faujasite type zeolite catalyst, preferably from $5 \times 10^{-4}$ gram to 0.2 gram per gram of the faujasite type zeolite catalyst. When the amount is less than $1 \times 10^{-4}$ gram per gram of the faujasite type zeolite catalyst, the selectivity of a p-substituted halobenzene derivative cannot effectively be improved, whereas, when the amount is more than 0.5 gram per gram of the faujasite type zeolite catalyst, the effect of increase in the amount of catalyst is small, and is therefore uneconomical.

In the present invention, the term "benzene derivative" means a compound in which a hydrogen atom of benzene is replaced by a substituent such as a halogen atom or an alkyl group. Such compounds are represented by, for example, halogenated benzenes and alkylated benzenes, more specifically monofluorobenzene, MCB, monobromobenzene, monoiodobenzene, toluene, ethylbenzene, etc. The halogenating reagent can be an elementary halogen such as chlorine, bromine, iodine or the like.

In the present invention, there is no particular restriction with regard to the kind of reactor used, the reaction method or the reaction conditions, so long as benzene and/or a benzene derivative contacts the catalyst in the liquid phase. For example, the reactor can be of the batch-wise, semi-batch-wise or continuous type. The catalyst can be used, for example, in the state of a fixed bed or a suspended bed.

The reaction may be conducted in the presence of a solvent which is inert to the halogenation reaction, such as carbon tetrachloride or the like. When such a solvent is used, the concentration of benzene and/or a benzene derivative can be 5 to 99% by weight, preferably 20 to 99% by weight. When the concentration is below 5% by weight, the chance of contact of the raw material with the catalyst is reduced and adequate conversion will not be obtainable. When a halogenating reagent is supplied continuously, the reagent can be accompanied by an inert gas such as nitrogen, helium, carbon dioxide or the like. When such an accompanying gas is used, the concentration of halogenating reagent can be 5 to 99% by volume, preferably 20 to 99% by volume.

When a batch-wise or semi-batch-wise reactor is used, the catalyst is used in most cases in a suspended bed in a raw material. The amount of catalyst can be 0.001 to 1 kg per liter of the raw material, preferably 0.005 to 0.1 kg per liter of the raw material. When the amount is less than 0.001 kg/liter, the load on the catalyst is too high and adequate conversion will not be obtainable. When the amount is more than 1 kg/liter, the effect of increase in the amount of catalyst is small. When the halogenating reagent is supplied continuously, the amount of halogenating reagent supplied can be expressed as the amount of halogenating reagent per unit time per unit weight of the zeolite. It can be 1 to 1,500 mole per hour per kg of the catalyst, preferably 10 to 800 mole per hour per kg of the catalyst. When the amount of halogenating agent is less than 1 mole per hour per kg of the catalyst, an adequate productivity rate of halogenated benzene cannot be obtained. When the amount exceeds 1,500 mole per hour per kg of catalyst, the amount of unreacted halogenating reagent increases, and is therefore uneconomical.

When a continuous reactor is used, the amount of liquid raw material supplied can be expressed as a amount of liquid raw material per unit time per unit weight of the zeolite and can be 0.5 to 300 liters per hour per kg of the catalyst, preferably 2 to 100 liters per hour per kg of the catalyst. The other reaction conditions are the same as those employed when a batch-wise or semi-batch-wise reactor is used.

In the present invention, there is no particular restriction with regards to the reaction temperature and the reaction pressure so long as benzene and/or a benzene derivative is in the liquid phase. When the reaction temperature is higher than the boiling point of benzene and/or a benzene derivative, halogenation in the liquid phase can be effected by increasing the reaction pressure. The reaction temperature is preferably 0° to 200° C., more preferably 20° to 150° C. When the temperature is lower than 0° C., an adequate reaction rate cannot be obtained. When the temperature exceeds 200° C., the selectivity of a p-substituted halobenzene derivative is low.

According to the present invention, a p-substituted halobenzene derivative which is very valuable in industry can be obtained by halogenation of benzene and/or a benzene derivative in the liquid phase, at a higher selectivity than in known processes with the same activity (rate and conversion). In case of the production of substituted halobenzene derivatives, isomerization reaction and recycling use of o-isomers are not usually conducted, because the isomerization reaction itself is very difficult, and in addition, m-isomers are largely produced by isomerization of o-isomers due to equilibrium. Consequently, even though the increase in p-isomers is a little, the amount of by-product o-isomers and the like, which are less valuable in industry, is reduced significantly, whereby p-isomers are easily separated and purified and the production cost of p-isomers are reduced greatly. Therefore, the present invention has a very high industrial significance.

EXAMPLES

The present invention will be explained in more detail below by way of Examples. However, the present invention is in no way restricted to these Examples. The terms "conversion" and "selectivity" used in the Examples refer to values calculated by the following formulations, respectively.

$$\text{Conversion (\%)} = \frac{\text{amount (mole) of benzene and/or benzene derivative fed} - \text{amount (mole) of benzene and/or benzene derivative unreacted}}{\text{amount (mole) of benzene and/or benzene derivative fed}} \times 100$$

$$\text{Selectivity (\%)} = \frac{\text{amount (mole) of desired product produced}}{\text{total amount (mole) of all products produced}} \times 100$$

EXAMPLES 1 TO 6

In a 1-liter porcelain beaker, 4.29 g of sodium chloride was dissolved in 150 ml of distilled water. This solution was maintained at 95° C. with a hot bath, and 10 g of Na-Y type zeolite (manufactured by Toyo Soda Manufacturing Co., Ltd.) having a $SiO_2/Al_2O_3$ ratio of 5.5 was added to and mixed with the solution under thorough stirring with an agitating blade made of glass. The mixture was then subjected to evaporation to dryness on the hot bath. Then, the resultant solid was dried for 15 hours in an oven held at 130° C., after which it was calcined for 3 hours at 540° C. in an air flow to obtained a Na-Y type zeolite catalyst having 30 wt% of NaCl.

Using this obtained catalyst and sulfur monochloride as a sulfur-containing compound, liquid phase chlorination of MCB was conducted. The chlorination was conducted using an ordinary semi-batch-wise reactor, A Pyrex ® reactor (inner diameter: 40 mm; height: 100 mm) having an internal volume of about 100 ml and equipped with a gas-introducing tube and a condenser was fed with 40 g of MCB and 0.016 g, 0.035 g, 0.069 g, 0.140 g, 0.245 g or 0.574 g of sulfur monochloride. Therein was suspended 1.4 g of the above-described zeolite catalyst.

While the reactor contents were being thoroughly stirred with a magnetic stirrer, 60 ml/min of a 50/50 mixture of chlorine gas and nitrogen gas was blown into the reactor i.e. at a rate of 30 ml/min of chlorine gas. The reaction temperature was controlled at 100° C. by heating the reactor with an oil bath. After 3 hours from the start of blowing of the gas mixture, the reaction products were analyzed by means of gas chromatography. The results are shown in Table 1.

COMPARATIVE EXAMPLE 1

Using a NaCl-modified Na-Y type zeolite catalyst prepared in the same manner as in Example 1, liquid phase chlorination of MCB was conducted in the same way as in Example 1 except that no sulfur-containing compound was present in the reaction system. The results of reaction after 3 hours from the start of blowing of the gas mixture are shown in Table 1.

TABLE 1

| | Amount of $S_2Cl_2$ | | MCB Conversion (%) | Selectivity (%) | | |
|---|---|---|---|---|---|---|
| | (g) | (g/g-faujasite)[1] | | PDCB | ODCB[2] | Others[3] |
| Ex. | | | | | | |
| 1 | 0.016 | 0.008 | 64.8 | 86.5 | 12.5 | 1.0 |
| 2 | 0.035 | 0.017 | 64.5 | 87.3 | 11.7 | 1.0 |
| 3 | 0.069 | 0.033 | 62.6 | 88.3 | 10.8 | 0.9 |
| 4 | 0.140 | 0.066 | 60.8 | 88.3 | 10.7 | 1.0 |
| 5 | 0.245 | 0.116 | 60.8 | 88.7 | 10.3 | 1.0 |
| 6 | 0.574 | 0.272 | 60.3 | 88.6 | 10.0 | 1.4 |
| Comp. Ex. 1 | — | — | 62.6 | 85.2 | 13.6 | 1.2 |

[1]Weight of sulfur per unit weight of faujasite
[2]ODCB: o-Dichlorobenzene
[3]m-dichlorobenzene, trichlorobenzene

EXAMPLE 7

In this Example, 0.07 g of sulfur was dissolved in 15 ml of carbon disulfide, and 3 g of NaCl-modified Na-Y type zeolite prepared in Example 1 was added to the solution. Then, carbon disulfide contained in the solution was distilled off using an evaporator to prepare a NaCl-modified Na-Y type zeolite catalyst containing sulfur. In this case, the weight of sulfur per unit weight of faujasite was 0.033 g per gram of the faujasite.

Using 1.52 g of the catalyst thus obtained, liquid phase chlorination of MCB was effected in the same manner as in Example 1 except that no sulfur monochloride was used. The MCB conversion and the selectivity of PDCB measured after 3 hours from the start of blowing of the gas mixture were 65.0% and 88.8%, respectively.

EXAMPLE 8

Using a NaCl-modified Na-Y type zeolite prepared in the same manner as in Example 1, liquid phase chlorination of MCB was conducted at a reaction temperature of 80° C. in the presence of 0.083 g of thiophene in place of sulfur monochloride. In this case, the weight of sulfur per unit weight of the faujasite was 0.032 g per gram of the faujasite. The reaction conditions other than those described above were the same as in Example 1.

The results of reaction after 3 hours from the start of blowing of the gas mixture are shown in Table 2.

EXAMPLES 9 TO 11

Using a NaCl-modified Na-Y type zeolite catalyst prepared in the same manner as in Example 1, liquid phase chlorination of MCB was conducted in the same way as in Example 1 except that 0.108 g of diphenyl sulfide, 0.121 g of diphenylsulfoxide or 0.131 g of diphenylsulfone was present in place of sulfur monochloride. The results of reaction after 3 hours from the start of blowing of the gas mixture are shown in Table 2.

TABLE 2

| | Sulfur-containing compounds | | MCB Conversion (%) | Selectivity % | | |
|---|---|---|---|---|---|---|
| | Compounds | Amount[1] (g/g-faujasite) | | PDCB | ODCB[2] | Others[3] |
| Ex. | | | | | | |
| 8 | thiophene | 0.032 | 62.9 | 87.4 | 11.6 | 1.0 |
| 9 | diphenyl sulfide | 0.019 | 62.3 | 87.2 | 9.9 | 0.9 |
| 10 | diphenyl sulfoxide | 0.019 | 61.4 | 87.5 | 10.5 | 1.0 |
| 11 | diphenyl | 0.019 | 61.3 | 87.9 | 10.2 | 0.9 |

TABLE 2-continued

| Sulfur-containing compounds | | MCB | | | |
|---|---|---|---|---|---|
| Compounds | Amount[1] (g/g-faujasite) | Conversion (%) | Selectivity % | | |
| | | | PDCB | ODCB[2] | Others[3] |
| sulfone | | | | | |

[1] Weight of sulfur per unit weight of faujasite
[2] ODCB: o-Dichlorobenzene
[3] m-Dichlorobenzene, trichlorobenzene

EXAMPLE 12

Using, as a catalyst, 1.0 g of Na-Y type zeolite (manufactured by Toyo Soda Manufacturing Co., Ltd.), liquid phase chlorination of MCB was conducted in the same manner as in Example 1 except that 0.540 g of sulfur monochloride was present. The results of reaction after 3 hours from the start of blowing of the gas mixture are shown in Table 3.

COMPARATIVE EXAMPLE 2

Liquid phase chlorination of MCB was conducted in the same manner as in Example 12 except that no sulfur monochloride was present. The results of reaction after 3 hours from the start of blowing of the gas mixture are shown in Table 3.

TABLE 3

| | MCB Conversion (%) | Selectivity (%) | | |
|---|---|---|---|---|
| | | PDCB | ODCB[1] | Others[2] |
| Example 12 | 62.1 | 81.7 | 16.4 | 1.9 |
| Comparative Example 2 | 63.4 | 79.1 | 19.3 | 2.0 |

[1] ODCB: o-Dichlorobenzene
[2] m-Dichlorobenzene, trichlorobenzene

EXAMPLE 13

Liquid phase chlorination of MCB was conducted in the same manner as in Example 12 except that Na-X type zeolite (manufactured by Toyo Soda Manufacturing Co., Ltd.) having a $SiO_2/Al_2O_3$ ratio of 2.5 was employed as a catalyst in place of Na-Y type zeolite. The MCB conversion and the selectivity of PDCB measured after 3 hours from the start of blowing of the gas mixture were 38.1% and 73.8%, respectively.

COMPARATIVE EXAMPLE 3

Liquid phase chlorination of MCB was conducted in the same manner as in Example 13 except that no sulfur monochloride was present. The MCB conversion and the selectivity of PDCB measured after 3 hours from the start of blowing of the gas mixture were 37.2% and 72.0%, respectively.

COMPARATIVE EXAMPLES 4 AND 5

Using, as a catalyst, Na-mordenite (manufactured by Toyo Soda Manufacturing Co., Ltd.) having a $SiO_2/Al_2O_3$ ratio of 15.0, liquid phase chlorination of MCB was respectively conducted in the same manner as in Example 12 in the presence and absence of sulfur monochloride. The results of reaction after 3 hours from the start of blowing of the gas mixture are shown in Table 4.

COMPARATIVE EXAMPLES 6 AND 7

According to the method described in U.S. Pat. No. 3,790,471 ZSM-5 zeolite was synthesized. The obtained zeolite was confirmed to be ZSM-5 by X-ray diffractometry (powder method) by radiation of copper Kα doublet. The ZSM-5 was calcined at 540° C. in an air flow and then subjected to an ion exchange treatment using an aqueous sodium chloride solution to obtain Na-ZSM-5 zeolite. This zeolite had the following formulation when expressed in terms of the mold ratio of oxides.

$1.05Na_2O.Al_2O_3.23.3SiO_2$

Using the Na-ZSM-5 zeolite as a catalyst, liquid phase chlorination of MCB was conducted in the same manner as in Example 12 in the presence and absence of sulfur monochloride. The results of reaction after 3 hours from the start of blowing of the gas mixture are shown in Table 4.

TABLE 4

| | Zeolites | Amount of $S_2Cl_2$[1] (g/g-zeolite) | MCB Conversion (%) | Selectivity (%) | | |
|---|---|---|---|---|---|---|
| | | | | PDCB | ODCB[2] | Others[3] |
| Comp. Ex. 4 | Na—mordenite | 0.032 | 27.9 | 68.3 | 27.6 | 4.1 |
| 5 | Na—mordenite | — | 48.1 | 71.3 | 26.7 | 2.0 |
| Comp. Ex. 6 | Na—ZSM-5 | 0.022 | 55.7 | 78.9 | 19.0 | 2.1 |
| 7 | Na—ZSM-5 | — | 52.0 | 79.3 | 17.8 | 2.9 |

[1] Weight of sulfur per unit weight of zeolite
[2] ODCB: o-Dichlorobenzene
[3] m-Dichlorobenzene, thichlorobenzene

EXAMPLE 14

Liquid phase chlorination of toluene was conducted in the same manner as in Example 1 except that the MCB in Example 1 was replaced by toluene. The toluene conversion and the selectivity of para-chlorotoluene measured after 3 hours from the start of blowing of the gas mixture were 54.2% and 66.8%, respectively.

COMPARATIVE EXAMPLE 8

Liquid phase chlorination of toluene was conducted in the same manner as in Example 14 except that no sulfur monochloride was added. The toluene conversion and the selectivity of para-chlorotoluene measured after 3 hours from the start of blowing of the gas mixture were 54.6% and 62.4%, respectively.

COMPARATIVE EXAMPLE 9

Liquid phase chlorination of MCB was conducted in the same manner as in Example 1 except that the zeolite catalyst used in Example 1 was replaced by 0.4 g of ferric chloride. The MCB conversion and the selectivity of PDCB measured after 3 hours from the start of blowing of the gas mixture were 64.7% and 68.5%, respectively.

EXAMPLE 15

Using a NaCl-modified Na-Y type zeolite prepared in the same manner as in Example 1 and 4-methylquinoline as a nitrogen-containing organic basic compound, liquid phase chlorination of MCB was conducted. The reaction method was just the same as in Example 1 except that 4-methylquinoline was used in place of sulfur monochloride. After 3 hours had passed from the start of blowing of the gas mixture, the product formed was analyzed. The results are shown in Table 5.

EXAMPLES 16 TO 19

Using a NaCl-modified Na-Y type zeolite catalyst prepared in the same manner as in Example 1, liquid phase chlorination of MCB was conducted in the same way as in Example 15 except that the amount of 4-methylquinoline was varied as follows: 0.086 g, 0.286 g, 0.573 g or 0.859 g. The results of reaction after 3 hours from the start of blowing of the gas mixture are shown in Table 5.

COMPARATIVE EXAMPLE 10

Using a NaCl-modified Na-Y type zeolite catalyst prepared in the same manner as in Example 1, liquid phase chlorination of MCB was conducted in the same way as in Example 15 except that no nitrogen-containing organic basic compound was present in the reaction system. The results of reaction after 3 hours from the start of blowing of the gas mixture are shown in Table 5.

TABLE 5

| | Amount of 4-methylquinoline | | MCB Conversion (%) | Selectivity (%) | | |
|---|---|---|---|---|---|---|
| | (g) | (g/g-faujasite)[1] | | PDCB | ODCB[2] | Others[3] |
| Ex. 15 | 0.057 | $5.6 \times 10^{-3}$ | 61.2 | 88.1 | 10.7 | 1.2 |
| 16 | 0.086 | $8.4 \times 10^{-3}$ | 61.3 | 88.4 | 10.4 | 1.2 |
| 17 | 0.286 | 0.028 | 62.5 | 88.5 | 10.4 | 1.1 |
| 18 | 0.573 | 0.056 | 60.4 | 88.4 | 10.4 | 1.2 |
| 19 | 0.859 | 0.084 | 59.6 | 88.6 | 10.1 | 1.3 |
| Comp. Ex. 10 | — | — | 62.6 | 85.2 | 13.6 | 1.2 |

[1]Weight of nitrogen per unit weight of faujasite
[2]ODCB: o-Dichlorobenzene
[3]m-Dichlorobenzene, trichlorobenzene

EXAMPLE 20 TO 30

Using a NaCl-modified Na-Y type zeolite catalyst prepared in the same manner as in Example 1, liquid phase chlorination of MCB was conducted in the same way as in Example 15 except that the 4-methylquinoline used in Example 15 was replaced by predetermined amounts of nitrogen-containing organic basic compounds such as those shown in Table 6. The results of reaction after 3 hours from the start of blowing of the gas mixture are shown in Table 6.

EXAMPLE 31

Using a NaCl-modified Na-Y type zeolite catalyst prepared in the same manner as in Example 1, liquid phase chlorination of MCB was conducted in the same way as in Example 15 except that the 4-methylquinoline used in Example 15 was replaced by 0.105 g of quinoline hydrochloride. The MCB conversion and the selectivity of PDCB measured after 3 hours from the start of blowing of the gas mixture were 62.0% and 87.1%, respectively.

TABLE 6

| | Nitrogen-containing organic basic compounds | Amount of nitrogen-containing organic basic compounds | | MCB Conversion (%) | Selectivity (%) | | |
|---|---|---|---|---|---|---|---|
| | | (g) | (g/g-faujasite)[1] | | PDCB | ODCB[2] | Others[3] |
| Example 20 | pyridine | 0.048 | $8.4 \times 10^{-3}$ | 60.1 | 87.0 | 12.0 | 1.0 |
| 21 | quinoline | 0.078 | $8.4 \times 10^{-3}$ | 60.8 | 87.6 | 11.2 | 1.2 |
| 22 | 8-oxyquinoline | 0.087 | $8.4 \times 10^{-3}$ | 60.2 | 88.3 | 10.4 | 1.3 |
| 23 | 2,4-dimethylquinoline | 0.094 | $8.4 \times 10^{-3}$ | 61.1 | 88.2 | 10.5 | 1.3 |
| 24 | diphenylamine | 0.102 | $8.4 \times 10^{-3}$ | 62.3 | 87.1 | 11.8 | 1.1 |
| 25 | 2-phenylimidazole | 0.086 | 0.017 | 60.5 | 87.2 | 11.7 | 1.1 |
| 26 | p-dimethylaminoazobenzene | 0.068 | 0.013 | 61.3 | 87.3 | 11.7 | 1.0 |
| 27 | n-dibutylamine | 0.052 | $5.6 \times 10^{-3}$ | 62.5 | 87.4 | 11.5 | 1.1 |
| 28 | n-tributylamine | 0.074 | $5.6 \times 10^{-3}$ | 60.0 | 87.5 | 11.4 | 1.1 |
| 29 | palmitylamine | 0.097 | $5.6 \times 10^{-3}$ | 60.6 | 87.0 | 11.8 | 1.2 |
| 30 | N,N—dimethylpalmitylamine | 0.108 | $5.6 \times 10^{-3}$ | 61.5 | 87.2 | 11.8 | 1.0 |

[1]Weight of nitrogen per unit weight of faujasite
[2]ODCB: o-Dichlorobenzene
[3]m-Dichlorobenzene, trichlorobenzene

EXAMPLE 32

Using, as a catalyst, 1.0 g of Na-Y type zeolite (manufactured by Toyo Soda Manufacturing Co., Ltd.), liquid phase chlorination of MCB was conducted in the same manner as in Example 15 except that 0.057 g of 4-methylquinoline was present. The results of reaction after 3 hours from the start of blowing of the gas mixture are shown in Table 7.

COMPARATIVE EXAMPLE 11

Liquid phase chlorination of MCB was conducted in the same manner as in Example 32 except that no 4-methylquinoline was present. The results of reaction after 3 hours from the start of blowing of the gas mixture are shown in Table 7.

TABLE 7

| | MCB Conversion (%) | Selectivity (%) | | |
|---|---|---|---|---|
| | | PDCB | ODCB[1] | Others[2] |
| Example 32 | 60.1 | 84.6 | 14.0 | 1.4 |
| Comparative Example 11 | 63.4 | 79.1 | 19.3 | 2.0 |

[1]ODCB: o-Dichlorobenzene
[2]m-Dichlorobenzene, trichlorobenzene

EXAMPLE 33

Liquid phase chlorination of MCB was conducted in the same manner as in Example 32 except that Na-X type zeolite (manufactured by Toyo Soda Manufacturing Co., Ltd.) having a $SiO_2/Al_2O_3$ ratio of 2.5 was used as a catalyst. The MCB conversion and the selectivity of PDCB measured after 3 hours from the start of blowing of the gas mixture were 38.3% and 74.8%, respectively.

COMPARATIVE EXAMPLE 12

Liquid phase chlorination of MCB was conducted in the same manner as in Example 33 except that no 4-methylquinoline was present. The MCB conversion and the selectivity of PDCB measured after 3 hours from the start of blowing of the gas mixture were 37.2% and 72.0%, respectively.

COMPARATIVE EXAMPLES 13 AND 14

Using, as a catalyst, Na-mordenite (manufactured by Toyo Soda Manufacturing Co., Ltd.) having a $SiO_2/Al_2O_3$ ratio of 15.0, liquid phase chlorination of MCB was conducted in the same manner as in Example 32 in the presence or absence, respectively, of 4-methylquinoline. The results of reaction after 3 hours from the start of blowing of the gas mixture are shown in Table 8.

COMPARATIVE EXAMPLES 15 AND 16

Using the Na-ZSM-5 zeolite as a catalyst prepared in the same manner as in Comparative Examples 6 and 7, liquid phase chlorination of MCB was conducted in the same manner as in Example 32 in the presence and absence of 4-methylquinoline. The results of reaction after 3 hours from the start of blowing of the gas mixture are shown in Table 8.

COMPARATIVE EXAMPLES 17 AND 18

Using, as a catalyst, 4.0 g of Ca-A type zeolite (manufactured by Toyo Soda Manufacturing Co., Ltd., trade name: "Zeolam A-5") having a $SiO_2/Al_2O_3$ ratio of 2.0, liquid phase chlorination of MCB was conducted in the same manner as in Example 32 in the presence or absence, respectively, of 4-methylquinoline. The results of reaction after 3 hours from the start of blowing of the gas mixture are shown in Table 8.

TABLE 8

| | Zeolites | Amount of[1] 4-methylquinoline (g/g-zeolite) | MCB Conversion (%) | Selectivity (%) | | |
|---|---|---|---|---|---|---|
| | | | | PDCB | ODCB[2] | Others[3] |
| Comparative Example 13 | Na—mardenite | $7.8 \times 10^{-4}$ | 4.3 | 69.8 | 27.6 | 2.6 |
| Comparative Example 14 | Na—mordenite | — | 48.1 | 71.3 | 26.7 | 2.0 |
| Comparative Example 15 | Na—ZSM-5 | $5.4 \times 10^{-4}$ | 5.7 | 78.9 | 18.9 | 2.2 |
| Comparative Example 16 | Na—ZSM-5 | — | 52.0 | 79.3 | 17.8 | 2.9 |
| Comparative Example 17 | Ca—A type | $2.5 \times 10^{-3}$ | 2.6 | 66.7 | 30.3 | 3.0 |
| Comparative Example 18 | Ca—A type | — | 50.2 | 68.8 | 28.3 | 2.9 |

[1]Weight of nitrogen per unit weight of zeolite
[2]ODCB: o-Dichlorobenzene
[3]m-Dichlorobenzene, trichlorobenzene

EXAMPLE 34

Liquid phase chlorination of toluene was conducted in the same manner as in Example 15 except that the MCB used in Example 15 was replaced by toluene. The toluene conversion and the selectivity of para-chlorotoluene measured after 3 hours from the start of blowing of the gas mixture were 53.8% and 67.1%, respectively.

COMPARATIVE EXAMPLE 19

Liquid phase chlorination of toluene was conducted in the same manner as in Example 34 except that no 4-methylquinoline was added. The toluene conversion and the selectivity of para-chlorotoluene measured after 3 hours from the start of blowing of the gas mixture were 54.6% and 62.4%, respectively.

What is claimed is:

1. A process for the production of parahalogenated holobenzenes or parahalogented alkylbenzenes comprising:

reacting, in liquid phase, at least one number selected from the group consisting of benzene, an alkyl benzene and a halogenated benzene, with elementary halogen at a reaction temperature of from 0° C. to 200° C., utilizing a faujasite zeolite as catalyst, in the presence of a co-catalyst selected from the group consisting of sulphur-containing compounds selected from the group consisting of sulfur, inorganic compounds containing a divalent sulfur atom and organic compounds containing a sulfur atom, and nitrogen-containing organic basic compounds selected from the group consisting of nitrogen-containing heterocyclic compounds, salts of nitrogen-containing heterocyclic compounds, aliphatic amines, salts of aliphatic amines, aromatic amines. salts of aromatic amines and mixtures therof.

2. The process according to claim 1, wherein the basicity constant of said nitrogen-containing organic basic compounds ranges from $1 \times 10^{-14}$ to $1 \times 10^{-1}$ (in 25° water.)

3. The process according to claim 1, wherein a sulfur-containing compound is employed in an amount of from $1 \times 10^{-4}$ gram to 1.0 gram in terms of the weight of sulfur atom per gram of the faujasite type zeolite.

4. The process according to claim 1, wherein a nitrogen-containing organic basic compounds is employed in an amount of from $1 \times 10^{-4}$ gram to 0.5 gram in the term of the weight of nitrogen atom per gram of the faujasite type zeolite.

5. A process according to claim 1, wherein said faujasite zeolite is selected from the group consisting of X zeolite and Y zeolite.

6. A process according to claim 1, wherein the X zeolite and the Y zeolite are modified by a salt of at least one member selected from the group consisting of alkyline metals, alkyine earth metals and rare earth metals.

7. A process according to claim 1, wherein said sulphur-containing compounds are selected from the group consisting of sulfur halides, thiophenes, sulfides, sulfoxides and sulfones.

8. A process according to claim 1, further comprising:

modifying said faujasite zeolite by at least one substance selected from the group consisting of sulphur-containing compounds selected from the group consisting of sulfur, inorganic compounds containing a divalent sulfur atom and organic compounds containing a sulfur atom, and nitrogen-containing organic basic compounds selected from the group consisting of nitrogen-containing heterocyclic compounds, salts of nitrogen-containing heterocyclic compounds, aliphatic amines, salts of aliphatic amines, aromatic amines, salts of aromatic amines and mixtures thereof.

* * * * *